US012735696B2

(12) United States Patent
Stroeder et al.

(10) Patent No.: US 12,735,696 B2
(45) Date of Patent: Sep. 15, 2026

(54) METHOD FOR ISOLATING HIGHLY PURE NUCLEIC ACID WITH MAGNETIC PARTICLES

(71) Applicant: QIAGEN GMBH, Hilden (DE)

(72) Inventors: Jasper Stroeder, Düsseldorf (DE); Corinna Hochstein, Düsseldorf (DE)

(73) Assignee: QIAGEN GMBH, Hilden (DE)

( * ) Notice: Subject to any disclaimer, the term of this patent is extended or adjusted under 35 U.S.C. 154(b) by 0 days.

(21) Appl. No.: 19/196,130

(22) Filed: May 1, 2025

(65) Prior Publication Data

US 2025/0263688 A1 Aug. 21, 2025

Related U.S. Application Data

(63) Continuation of application No. 16/469,559, filed as application No. PCT/EP2017/082797 on Dec. 14, 2017.

(30) Foreign Application Priority Data

Dec. 15, 2016 (EP) .................................... 16204386

(51) Int. Cl.
*C12N 15/10* (2006.01)
*G01N 1/34* (2006.01)
*G01N 1/40* (2006.01)

(52) U.S. Cl.
CPC ........... *C12N 15/1013* (2013.01); *G01N 1/34* (2013.01); *G01N 1/40* (2013.01)

(58) Field of Classification Search
CPC ........ G01N 1/40; G01N 1/34; C12N 15/1013; C12N 15/1006
USPC ...................................................... 536/25.41
See application file for complete search history.

(56) References Cited

U.S. PATENT DOCUMENTS 6,673,631 B1 * 1/2004 Tereba ............... C12N 15/1013 436/526
2009/0191566 A1 * 7/2009 McKernan ......... C12N 15/1006 435/6.16

FOREIGN PATENT DOCUMENTS

| | | | |
|---|---|---|---|
| CN | 102264901 | A | 11/2011 |
| CN | 102421898 | A | 4/2012 |
| WO | 1996/09379 | A1 | 3/1996 |
| WO | 1999/58664 | A1 | 11/1999 |
| WO | 2001/71732 | A2 | 9/2001 |
| WO | 2003/091452 | A1 | 11/2003 |
| WO | 2004/090132 | A2 | 10/2004 |
| WO | 2005/021748 | A1 | 3/2005 |
| WO | 2010/072821 | A1 | 7/2010 |
| WO | 2010/130402 | A1 | 11/2010 |

OTHER PUBLICATIONS

International Search Report issued in International Application No. PCT/EP2017/082797, dated Jan. 29, 2018.
Hawkins et al., "DNA purification and isolation using a solid-phase," Nucleic Acids Research (1994) 22(21):4543-4544.
Giolai et al., "Targeted capture and sequencing of gene-sized DNA molecules," Biotechniques 6(61):315-322 (2016).

* cited by examiner

*Primary Examiner* — Ganapathy Krishnan
(74) *Attorney, Agent, or Firm* — MEDLER FERRO WOODHOUSE & MILLS PLLC

(57) ABSTRACT

Subject of the invention is a method for isolating nucleic acid from a sample solution, wherein the nucleic acid is separated from the sample solution by adsorption to magnetic particles, followed by separation of the magnetic particles with the nucleic acid adsorbed thereto from the sample solution by application of a magnetic field, followed by at least one washing step (w), comprising (w1) suspending the magnetic particles with the nucleic acid adsorbed thereto in a washing solution, which is an aqueous solution, which has a total salt concentration below 100 mM and does not comprise an organic solvent,
(w2) incubating the magnetic particles with the nucleic acid adsorbed thereto in the washing solution, and
(w3) separating the magnetic particles with the nucleic acid adsorbed thereto from the washing solution.

The invention also relates to use of an aqueous solution, which has a total salt concentration below 100 mM and does not comprise an organic solvent, as a washing solution for washing magnetic particles with nucleic acid adsorbed thereto.

14 Claims, 4 Drawing Sheets pCMVβ

Water:

pUC21

Water:

Elution:

METHOD FOR ISOLATING HIGHLY PURE NUCLEIC ACID WITH MAGNETIC PARTICLES

The invention relates to methods for isolating nucleic acid from a sample solution, wherein the nucleic acid is separated from the sample solution by adsorption to magnetic particles, followed by separation of the magnetic particles with the nucleic acid adsorbed thereto from the sample solution by application of a magnetic field. Subject of the invention are also uses of washing buffers in such methods.

STATE OF THE ART

Obtaining DNA or RNA sufficiently free of contaminants for molecular biological applications is difficult in view of the complex systems in which the DNA or RNA is typically found. These systems, such as biological samples, such as tissue, cells from body fluids such as blood, cultured cells, or artificial systems such as agarose gels or PCR reaction samples, typically include significant quantities of contaminants from which the DNA or RNA of interest must be separated before being used in a molecular biological procedure.

Conventional protocols for obtaining DNA or RNA from cells entail suspending the cells in a solution and using enzymes and/or chemicals, to lyse the cells, thereby releasing the nucleic acid contained within the cells into the resulting lysate solution. For isolation of RNA, the conventional lysis and solubilization procedures that are applied for releasing DNA include additional measures for inhibition of ribonucleases and contaminants to be separated from the RNA including DNA.

Silica materials, including glass particles, such as glass powder, silica particles, and glass microfibers prepared by grinding glass fiber filter papers, and including diatomaceous earth, are used in the art in combination for example with aqueous solutions of chaotropic salts to separate DNA from other substances and render the DNA suitable for use in molecular biological procedures.

Glass particles, silica particles, silica gel, and mixtures of the above have been configured in various different forms to produce matrices capable of reversibly binding nucleic acid materials by adsorption to the surface when placed in contact with a medium containing such materials in the presence of binding inducing agents like chaotropic agents. Such matrices are designed to remain adsorbed to the nucleic acid material while the matrix is exposed to an external force such as centrifugation or vacuum filtration to separate the matrix and nucleic acid material adsorbed thereto from the remaining media components. The nucleic acid material usually is then eluted from the matrix by exposing the matrix to an elution solution, such as water or an elution buffer. Numerous commercial sources offer silica-based matrices designed for use in centrifugation and/or filtration isolation systems (e.g. the QiaPrep®, QIAamp® and AllPrep® lines of nucleic acid isolation systems from QIAGEN, Hilden, Germany).

Magnetically responsive particles (herein referred to as 'magnetic particles') and methods for using them have been developed for the isolation of nucleic acid materials. Several different types of magnetic particles designed for use in nucleic acid isolation are described in the literature and are available from commercial sources. Such magnetic particles generally fall into either of two categories, those designed to reversibly bind nucleic acid materials directly, and those designed to do so indirectly, i.e. through at least one intermediary substance. The intermediary substance is referred to herein as a 'label'. For example, one such commonly employed label, biotinylated oligonucleotide deoxythymidine (oligo-dT), forms hydrogen bonds with the polyadenosine tails of mRNA molecules in a medium.

Magnetic particles which bind nucleic acids directly are often based on silica, such as magnetically responsive siliceous-oxide coated particles (also referred to as magnetic beads; e.g. available under the trademarks MagAttract® from QIAGEN, Hilden, Germany; or MagneSil® from Promega, Madison, USA). Nucleic acids adhere to these particles in the presence of binding inducing agent like a chaotropic salt, e.g. guanidinium hydrochloride or guanidinium isothiocynate, alone or in combination with a binding additive, like an alcohol; e.g. ethanol. After separation of the particles, if desired, elution of the adsorbed nucleic acids from the particles may be achieved easily by incubation of the particles in water or a buffer with low ionic strength.

Several different methods of automated separation of magnetic particles are known from the art. One method is to insert a magnetic or magnetizable device, such as a rod, into the medium containing the magnetic particles, binding the magnetic particles to the magnetic or magnetizable device, and removing the magnetic or magnetizable device. Another method is to bring a magnetic or magnetizable device into spatial proximity to the container which contains the medium and the magnetic particles. The magnetic particles bind to the container wall and the medium can be removed without carry-over of magnetic particles.

WO 01/71732 A2 discloses methods for producing magnetic particles based on silica and iron oxide and their use in isolating biological molecules. A molecule of interest, such as nucleic acids like DNA and/or RNA, is adhered to the magnetic particles, usually followed by separation of the magnetic particles from the solution, washing and elution of the molecules. Binding of nucleic acids to the magnetic particles is preferably carried out in an aqueous solution comprising a high concentration of chaotropic salt and/or a low molecular weight alcohol, such as isopropanol or ethanol. Elution of the nucleic acid from the magnetic particles is preferably carried out with a low salt buffer. In such a process, the desired molecule, such as the nucleic acid, usually is desired to be obtained in relatively pure form. Thus, the chaotropic salt from the starting solution needs to be removed as much as possible. In order to achieve this, washing steps typically are carried out with one or more buffers preferably having a lower salt concentration than the starting solution. In order to maintain binding conditions in the multiple washing steps, the buffers generally comprise relatively high levels of ethanol, such as 70% (w/w). In a final washing step, pure ethanol may be used. After the final washing step it is common that the sample with magnetic particles and the molecule bound thereto is left standing at room temperature to dry, such that ethanol is removed by volatilization. However, in view of the high salt concentration of the starting material, and since washing buffers usually comprise a salt, the nucleic acid obtained according to such a method may still comprise residual salt. Further, evaporation of ethanol by drying is relatively time-consuming. In a standard process, evaporation often does not fully dry the sample and deplete it completely from ethanol. Additional washing steps and extensive drying may further increase the purity, but such a process would be even more time consuming and not be convenient any more for routine use.

WO 03/091452 A1 discloses a method for isolating nucleic acid from biological materials with magnetic particles. In order to prevent aggregate formation of the magnetic particles, specific washing solutions are used comprising lower alcohols. Further, the washing solutions may comprise chaotropic salts in relatively high amounts. Thus, the problem remains that the final nucleic acid product may comprise undesired salt or alcohol impurities.

WO 2005/021748 A1 discloses a further method for isolating biopolymers from aqueous solution with magnetic particles. The biopolymers are bound to magnetic particles from aqueous solution comprising salt and ethanol, followed by washing and elution. In order to improve the handling of the magnetic particles, an additive, such as polyethylene glycol is added. Washing steps are carried out with washing solutions comprising relatively high amounts of chaotropic salt and ethanol, followed by drying for ethanol removal.

Commercial kits for isolating nucleic acids from various sources and of various sizes with magnetic particles are for instance available from Qiagen, Hilden, Germany, under the trademark MagAttract®. The basic protocol, which is for example used in the MagAttract® HMW DNA Kit, is similar as described further above and comprises steps of binding DNA from aqueous solution in the presence of chaotropic salts and ethanol, followed by washing steps and final elution of DNA. The standard washing steps are carried out in the presence of relatively high salt concentration and ethanol. However, in order to remove salt and ethanol impurities which might interfere with subsequent downstream processes from the DNA product a final washing step is included, in which the pellet of magnetic particles with DNA bound thereto, when fixed to the wall of the sample tube by magnetic force, is just briefly rinsed with water. When proceeding accordingly, the water mostly contacts only the surface of the pellet adhered to the sample tube wall. According to the handbook, it is important that the water is not added directly onto the particles, but carefully pipetted into the sample tube against the side facing away from the magnetic particle pellet with bound DNA. Further, all pipetting steps shall be performed carefully to avoid disturbing the fixed magnetic particle pellet. These precautions are considered necessary because the rinsing step is in fact carried out under non-binding conditions, under which the nucleic acid is normally eluted from the particles. Thus, it is expected that intensive washing results in a loss of nucleic acids. Accordingly, in the same protocol it is noted that pure water can be used as the elution buffer. However, since the magnetic particle pellet, which is fixed to the tube wall by magnetic force, is not disaggregated under such a rather superficial washing procedure, and since this water rinsing is only applied for a short time only, a portion of the salt and/or ethanol may remain trapped in the magnetic particle pellet and, thereby, cannot be removed. Thus, it is desired to further improve the purity of the finally purified and isolated nucleic acid, either in pure form or dissolved.

US2009/0191566 A1 discloses a method for isolating biopolymers from aqueous solution with magnetic particles by affinity binding. The magnetic beads are modified with a first and a second functional group. Specifically, the functional groups are affinity ligands such as oligo-dT or streptavidin, which specifically bind target molecules such as mRNA or biotin-labelled DNA. As is common practice in the state of the art, the wash buffer must have a “sufficiently high salt concentration”, such that “the nucleic acid does not elute off the solid phase carrier, but remains bound to the microparticles”. Consequently, usually the salt has to be removed in a subsequent purification step to avoid impairment in downstream applications.

Hawkins et al, Nucl. Acids Res. 1994, Vol. 22, Nr. 21, 4543-4544, discloses a method for DNA purification with carboxyl-coated magnetic beads. The document discloses a final wash step using a comparatively low salt concentration. However, the factual salt concentration in said final washing step actually is relatively high due to the remainders of a preceding wash step with a quite high salt concentration of 5M NaCl. Overall, the process is inefficient because the washing step reduces the yield to about 80%. Therefore, the method is not suitable for quantitative nucleic acid isolation.

WO2004/090132 A2 discloses a method for isolating genomic nucleic acid with solid phase carriers comprising functional groups for binding the nucleic acids. Specifically, magnetic beads are used which are modified with carboxyl groups. The disclosed properties of the wash buffers are basically the same as disclosed in US2009/0191566A1 as discussed above. Again, the wash buffer should have a sufficiently high salt concentration, such that the nucleic acid remains bound to the microparticles and as a consequence the salt usually will have to be removed in a subsequent purification step.

WO99/58664 describes a similar process for isolating nucleic acids with carboxyl-coated magnetic beads. Suitable buffers should have properties and relatively high salt concentration as described above for US2009/0191566A1 or WO2004/090132, in order to ensure that nucleic acids remain bound to the microparticles.

Overall, there is a continuous need in the prior art for a simple and efficient process for isolating nucleic acids with magnetic particles, in which the level of impurities in the finally isolated nucleic acid, in particular DNA, is low.

Problem Underlying the Invention

The problem underlying the invention is to provide a method for isolating nucleic acid from a sample solution, which overcomes the above-mentioned drawbacks. Specifically, the problem underlying the invention is to provide an improved method for isolating nucleic acid, in which the finally isolated nucleic acid has a high purity, whether in pure form or dissolved. The nucleic acid when not obtained in pure form but as an isolation product should basically contain, preferably even consist of the elution buffer and the desired nucleic acid. The level of impurities, such as salt and organic solvent, such as alcohol like ethanol, should be low.

It is a further problem underlying the invention to provide a simple method for isolating highly pure nucleic acid. The process shall comprise only a small number of process steps, which should be carried out relatively easily and conveniently. Thus, the method shall be applicable for routine use in standard laboratory practice as well as in automated form, i.e. with robots and work stations. The method shall be available with standard laboratory materials and devices.

DISCLOSURE OF THE INVENTION

Surprisingly, it was found that the problem underlying the invention is overcome by methods according to the claims. Further embodiments of the invention are outlined throughout the description.

Subject of the invention is a method for isolating nucleic acid from a sample solution, wherein the nucleic acid is separated from the sample solution by adsorption to magnetic particles, followed by separation of the magnetic particles with the nucleic acid adsorbed thereto from the sample solution by application of a magnetic field, followed by at least one washing step (w), comprising (w1) suspending the magnetic particles with the nucleic acid adsorbed thereto in a washing solution, which is an aqueous solution, which has a total salt concentration below 100 mM and does not comprise an organic solvent, (w2) incubating the magnetic particles with the nucleic acid adsorbed thereto in the washing solution, and (w3) separating the magnetic particles with the nucleic acid adsorbed thereto from the washing solution.

The inventive method is directed in particular to isolating nucleic acid. As used herein, "isolating nucleic acid" relates to any method in which contaminants and impurities are removed from the target nucleic acid and/or in which the concentration of the nucleic acid is enhanced.

The term "nucleic acid" or "nucleic acids" as used herein, in particular refers to a polymer comprising ribonucleosides and/or deoxyribonucleosides that are covalently bonded, typically by phosphodiester linkages between subunits, but in some cases by phosphorothioates, methylphosphonates, and the like. Nucleic acids include, but are not limited to all types of DNA and/or RNA, e.g. gDNA; plasmid DNA, circular DNA; circulating DNA; hnRNA; mRNA; noncoding RNA (ncRNA), including but not limited to rRNA, tRNA, lncRNA (long non coding RNA), lincRNA (long intergenic non coding RNA), miRNA (micro RNA), siRNA (small interfering RNA), snoRNA (small nucleolar RNA), snRNA (small nuclear RNA) and stRNA (small temporal RNA), piRNA (piwi interacting RNA), tiRNA (transcription initiation RNA), PASR (promoter associated RNA), CUT (cryptic unstable transcripts), extracellular or circulating RNA; fragmented nucleic acid; nucleic acid obtained from subcellular organelles such as mitochondria or chloroplasts; and nucleic acid obtained from microorganisms, parasites, or DNA or RNA viruses that may be present in a biological sample. Synthetic nucleic acid sequences that may or may not include nucleotide analogues that are added or "spiked" into a biological sample are also within the scope of the invention. Small RNA or the term small RNA species in particular refers to RNA having a length of less than 500 nt. According to one embodiment, the nucleic acid is DNA.

A sample may comprise more than one type of nucleic acid. Depending on the intended use, it may be desirous to isolate all types of nucleic acids from a sample ((e.g. DNA and RNA) or only certain types or a certain type of nucleic acid (e.g. only RNA but not DNA or vice versa or DNA and RNA are supposed to be obtained separately). All these variants are within the scope of the present invention. Suitable methods for isolating either DNA or RNA or both types of nucleic acids in parallel are known in the prior art.

The term "sample" is used herein in a broad sense and is intended to include a variety of sources that contain nucleic acids. The sample may be a biological sample but the term also includes other, e.g. artificial samples which comprise nucleic acids. Exemplary samples include, but are not limited to, body fluids in general, whole blood; serum; plasma; red blood cells; white blood cells; buffy coat; swabs, including but not limited to buccal swabs, throat swabs, vaginal swabs, urethral swabs, cervical swabs, throat swabs, rectal swabs, lesion swabs, abcess swabs, nasopharyngeal swabs, and the like; urine; sputum; saliva; semen; lymphatic fluid; liquor; amniotic fluid; cerebrospinal fluid; peritoneal effusions; pleural effusions; fluid from cysts; synovial fluid; vitreous humor; aqueous humor; bursa fluid; eye washes; eye aspirates; plasma; serum; pulmonary lavage; lung aspirates; and tissues, including but not limited to, liver, spleen, kidney, lung, intestine, brain, heart, muscle, pancreas, cell cultures, as well as lysates, extracts, or materials obtained from any cells and microorganisms and viruses that may be present on or in a sample and the like. Materials obtained from clinical or forensic settings that contain nucleic acids are also within the intended meaning of the term sample. Furthermore, the skilled artisan will appreciate that lysates, extracts, or materials or portions thereof obtained from any of the above exemplary samples are also within the scope of the term sample. Preferably, the sample is a biological sample derived from a human, animal, plant, bacteria or fungi. In particular, the term "sample" refers to a nucleic acid containing sample which also comprises proteins. Preferably, the sample is selected from the group consisting of cells, tissue, bacteria, virus and body fluids such as for example blood, blood products such as buffy coat, plasma and serum, urine, liquor, sputum, stool, CSF and sperm, epithelial swabs, biopsies, bone marrow samples and tissue samples, preferably organ tissue samples such as lung and liver. Preferably, the sample is selected from whole blood and blood products such as buffy coat, serum or plasma.

The nucleic acid may also be an artificially synthesized nucleic acid, for example from a PCR reaction. The sample solution used in the process could be obtained directly from the biological material, for example by lysis of cells or tissue or by fractionation and/or pre-treatment of body liquids. Alternatively, the sample solution could be obtained from a nucleic acid processing method, which may be a method for purification, synthesis or modification, such as PCR or purification from agarose gel.

In a preferred embodiment, the nucleic acid isolated in the inventive method is obtained in pure form, or essentially pure form or it may be dissolved. Preferably, only unavoidable impurities are comprised in the pure nucleic acid or in the dissolved nucleic acid product. Preferably, the purity of the isolated nucleic acid is at least 90%, more preferably at least 90%, and most preferably more than 99% or 99.5% by weight, referring to the pure nucleic acid or based on all solids in the dissolved nucleic acid product excluding solid additives from the elution solution.

In the inventive process, the nucleic acid preferably is separated from the sample solution by binding to magnetic particles. Thus, the nucleic acid must be accessible to the magnetic particles for binding. In a preferred embodiment, the sample solution is an aqueous solution in which the nucleic acid is normally dissolved or suspended. In case a preceding starting material does not comprise nucleic acid directly accessible for binding, pre-treatment steps are preferably carried out, such as lysis and/or disruption of biological material, such as cells or tissues.

The nucleic acid is separated from the solution by adsorption to the magnetic beads. In the inventive method, binding of the nucleic acid to the magnetic particles is expected to be mainly adsorptive. In this case, the binding usually is non-covalent and reversible. Adsorption is the adhesion of nucleic acid molecules to the surface of the magnetic beads. In the binding step, conditions preferably are adjusted such that the nucleic acid binds to the magnetic particles, typically by adding one or more chaotropic salts, non-chaotropic salts and/or low molecular weight alcohol ("binding-conditions").

In the inventive method, the binding force between the nucleic acid and the magnetic particles in step (w) of the inventive process is preferably only based on adsorption. Preferably, it is not based on other binding mechanisms, such as affinity chromatography or ion exchange chromatography. Affinity chromatography requires a highly specific interaction between two specific molecules, such as antigen and antibody, enzyme and substrate, or receptor and ligand, according to the key-lock-principle. Ion exchange chromatography is based on specific interactions of target molecules with charged ligands on the substrate surface. More preferably, the method is not based on specific interactions of nucleic acid with carboxyl groups attached to the magnetic particles.

In a preferred embodiment, the magnetic particles are not modified with ligands, especially organic ligands. Preferably, no ligands are attached to the surface of the particles. Thus, it is preferred that the particles are not modified with affinity ligands, such as streptavidine or poly-dT. Further, it is preferred that the particles are not modified with ion exchange ligands, such as cation exchange ligands. More preferably, they are not modified with carboxyl-groups and/or do not comprise carboxyl-groups on the surface.

In another embodiment, the magnetic particles are bifunctional. This means that they are capable of adsorbing nucleic acids as a first functionality, but have a second functionality. For example, the adsorptive particles may be modified with affinity ligands, such that the second functionality would be affinity binding. This second functionality could be used for binding a substrate to the particles in a different binding step than during (w).

Separation of the magnetic particles with nucleic acid bound thereto from the sample solution is realized by application of a magnetic field. Typically, a magnetic field is applied outside the sample tube, such that magnetic particles are attracted to a defined location and accumulate there, for example on a side of the sample tube. Alternatively, a magnetic device can be inserted into the sample tube or close to the sample tube, to which the magnetic particles are adhered. For example, the device could be a magnetic rod. Preferably, in the binding step magnetic particles accumulate in the form of a pellet or cluster. After accumulating the magnetic particles with the nucleic acid bound thereto, they are separated from the sample solution, thereby removing the sample solution.

The inventive method comprises at least one washing step (w) which comprises at least sub-steps (w1), (w2) and (w3) as outlined above, which are carried out in consecutive order. Preferably, step (w) consists of sub-steps (w1) to (w3).

In sub-step (w1), the magnetic particles with the nucleic acid bound thereto are suspended in the washing solution. In this step, the magnetic particles with the nucleic acid bound thereto are normally detached from the predetermined location in which they were fixated by the magnetic field. Preferably, unless the particles are transferred into another tube the magnetic particles are fixated by the magnetic field such that they maintain contact with the liquid mixture in the tube. Normally, the magnetic field is inactivated before or during step (w1), such that the magnetic particles can be easily suspended in the washing solution. For example, the magnetic particles may be attached to the sample tube wall by the magnetic field or to a magnetic device within the tube, whereupon the magnetic field is switched off, removed or relocated and the magnetic particles are suspended in the washing solution. Preferably, single magnetic particles are distributed in the solution, such that any cluster or pellet is at least partly, preferably completely dispersed. This may be supported by gentle movement.

In a preferred embodiment, suspending the magnetic particles in the washing solution in step (w1) is supported by mild agitation, preferably in a vertical direction i.e. in more or less the same direction as the tube axis. In a highly preferred embodiment, the magnetic particles are attracted to a magnet in an elevated position in relation to the bottom of the tube and are dropped into the washing solution within the tube in step (w1) by switching off, removing or relocating the magnet. It was found that such mild agitation which in this preferred embodiment may be induced for example by the particles' movement through the washing solution to the bottom of the tube for example by gravity or a further, in particular light magnetic force applied below the elevated position, may support release of contaminants from the magnetic beads. Yet, the applied agitation should be chosen such that no significant release of the nucleic acid from the magnetic particles takes place. The gentle movement may for instance be achieved by a device being dipped into the liquid of the tube and moved up and down, like a magnetic rod or a PickPen® provided e.g. by BioControl. It is also suitable to suspend the magnetic particles by carefully rinsing them from the tube wall or from any kind of magnetic device that is dipped into the tube liquid with the washing solution once the magnetic device has been switched off, removed or relocated. Intensive agitation, i.e. in particular induced by a mechanical means like any kind of shaking device should be avoided.

Thus, preferably, the magnetic particles with the nucleic acid bound thereto are not subjected to a mechanical force. In a specifically preferred embodiment the magnetic particles with the nucleic acid bound thereto are not subjected to a mechanical force exerted oscillating and/or horizontally. Examples for devices exerting oscillating and/or horizontal mechanical force are the usually known laboratory vortexers or laboratory shakers. Manual shaking is usually also an example for such a force. Yet, a mild mechanical force exerted vertically, like gravity, may be applied as well. This may be realized for example by the magnetic beads being attached to the tube wall or to a magnetic device dipped in the liquid within the tube at an extended position and then switching off, removing or relocating the magnetic device. Due to the gravity the magnetic particles sink towards the bottom of the tube, decelerated depending on the viscosity of the liquid in the tube. In addition, a magnetic force preferably exerted vertically i.e. having more or less the same direction as the tube axis, may be applied. Yet, the strength of the magnetic field should be chosen such that the induced movement within the washing solution does not significantly release the nucleic acid from the magnetic particles. This may be realized with a magnetic device being positioned outside of the tube, for example at or under its bottom.

In the same way, preferably, the magnetic particles with the nucleic acid bound thereto are suspended in the washing solution without applying a mechanical force. In a specifically preferred embodiment the magnetic particles with the nucleic acid bound thereto are suspended in the washing solution without applying a mechanical force exerted oscillating and/or horizontally. Yet, a mild mechanical force exerted vertically, like gravity, may be applied when suspending the magnetic particles in the washing solution. In addition, a magnetic force preferably exerted vertically i.e. having more or less the same direction as the tube axis, may be applied.

Thus, the purity of the isolated nucleic acid may be increased further by such mild agitation. Further, it is preferred that there is no agitation, i.e. stirring or shaking, in incubation step (w2).

In a preferred embodiment, the magnetic particles with nucleic acid bound thereto in this washing step (w) are not subjected to mechanical force, in particular not strong mechanical force, which goes beyond mild agitation. It was found that mechanical forces, and in particular strong mechanical forces, may enhance release of nucleic acid from the magnetic particles. Specifically, the sample should not be stirred or shaken, in particular not be mechanically stirred or shaken, in the washing step (w).

The washing solution used in step (w1) is an aqueous solution. It is characterized by a salt concentration below 100 mM and by the absence of an organic solvent. Thereby, the washing solution is distinct from washing solutions commonly used in such processes with magnetic particles. The washing solution used according to the invention is unique, because in fact conditions are applied which are generally considered as "non-binding" conditions. Thus, washing steps in the prior art are always carried out with washing solutions under "binding conditions", which are adjusted for example with a high salt concentration of 1 M or higher. According to the prior art, the salt is often a chaotropic salt. Further, typical washing solutions used in the prior art comprise high amounts of organic solvent, especially ethanol or isopropanol. By adding one or more salts at high concentration and/or organic solvents, it shall be ensured in the processes of the prior art that the nucleic acid is not detached from the magnetic particles and thereby lost.

As outlined above, for example in the protocol related to the MagAttract® HMW DNA Kit, a final washing step is carried out, in which the magnetic particles with nucleic acids attached thereto are rinsed with pure water. However, the rinsing step is only carried out very briefly when magnetic particles are adhered in the form of a pellet to the sample tube wall. Care should be taken that the pellet is not disrupted or mechanically disturbed when the water is added at a different position in the tube. When proceeding accordingly, the rinsing water has no access to the interior of the magnetic particle pellet, such that the high salt and ethanol environment is basically maintained within the pellet. The method of the present invention is strikingly different because the magnetic particles with the nucleic acids bound thereto are suspended in the low-salt washing solution. In the prior art, it had been assumed that such a treatment would not be applicable for washing, because it should cause elution of nucleic acids from the particles. Surprisingly, it has been found according to the present invention that washing may be carried out in a suspension under such "non-binding" conditions, with a great increase in product purity, but without significant loss of nucleic acid. This is highly advantageous, because an efficient removal of salt, ethanol and/or other contaminants from the target nucleic acid can be achieved without significant reduction of the nucleic acid yield. Without being bound to theory, it is assumed that an intermediate state is formed, in which forces between the magnetic particles and nucleic acid molecules temporarily prevent release of the nucleic acid molecules from the particles. In contrast, in an equilibrium state, which is not reached in the inventive process, a significant loss of nucleic acid would be obtained. The inventive process is also highly advantageous, because a drying step for evaporating organic solvents, such as ethanol, although still possible, is not necessary any more. The inventive process correspondingly may save considerable time, because drying steps for removal of organic solvents, if carried out thoroughly, are relatively time-consuming.

As noted above, the total salt concentration of the washing solution is preferable below 100 mM. Such a concentration is in general insufficient for stable binding of nucleic acids to magnetic particles by adsorption. In contrast, low salt concentrations typically destabilize the non-covalent interactions between the magnetic particle surfaces and the polyanionic nucleic acid. In a preferred embodiment, the washing solution has a total salt concentration of below 50 mM, more preferably of below 25 mM or of below 10 mM. In another preferred embodiment, the washing solution does not comprise any salt. This means that salt has not been added to the washing solution. Thus, only unavoidably salt impurities like the ones already incorporated within the magnetic particle/nuclei acid complex may be comprised. Preferably, the washing solution is water, more preferably distilled water. In principle, including salt into the washing solution in a concentration of up to 100 mM is not required for stabilizing the magnetic particle/nucleic acid complex in washing step (w). However, a low amount of salt may be desired in the final product, for example in the form of a buffer substance for stabilizing the product or facilitating further use. Thus, the salt could be a buffer substance, such as TRIS (Tris(hydroxymethyl)aminomethan). The pH of the washing solution may be between 7 and 10, especially between 7.5 and 9.

In a preferred embodiment, the conditions in the liquid phase of the sample (the suspension) in step (w1), after addition of the washing solution, are essentially the same as in the washing solution used in step (w1), at least with respect to salt concentration and absence of an organic solvent. Therefore, it is preferred that before addition of the washing solution in step (w1), the sample does not comprise significant amounts of residual salt or organic solvent, which would significantly increase the salt concentration or level of organic solvent in the liquid phase. Therefore, it is preferred that the total salt concentration in the liquid phase, in the suspension of step (w1), after addition of the washing solution, is below 100 mM, more preferably of below 25 mM or of below 10 mM. Further, it is preferred that suspension does not comprise organic solvent, except for unavoidable impurities, for example below 2 wt. %. In a preferred embodiment, the salt concentration in the solution in the process step which is carried out directly before step (w) (or if step (w) is repeated, before the last step (w)) is not more than 2 M, preferably not more than 1 M.

If desired, the washing solution may comprise additives different from salts and organic solvents, such as compounds for stabilizing nucleic acids, such as proteases or complexing agents like EDTA. In a preferred embodiment, the washing solution consists of water and optionally salt at a concentration of below 100 mM, and optionally such additives.

The washing solution in washing step (w) preferably does not comprise an organic solvent. Thus, in a preferred embodiment it does not comprise low molecular weight alcohols having 1 to 5 carbon atoms, such as ethanol or isopropanol. Thus, the washing solution is distinct from typical conventional washing solutions used in such processes which comprise ethanol or isopropanol. In a specific embodiment, the washing solution does not comprise an organic compound at all. Preferably, the washing solution does not comprise a detergent.

It is highly preferred that washing step (w) is the final washing step in the inventive method. In a specifically preferred embodiment, the washing step (w) is directly followed by the final elution of the nucleic acid from the magnetic particles. In general, it is preferred that the washing solution used in step (w) is identical to the elution solution. Yet, it is also possible to release the nucleic acid from the magnetic particles after the washing step (w) not in a separate elution step but in the subsequent downstream procedure.

In a preferred embodiment of the invention, washing step (w), i.e. the combination of sub-steps (w1) to (w3), is carried out in 5 minutes or less, preferably 2 minutes or less. This means that it should be carried out in the defined time range. In other words, the time in which the magnetic particles with nucleic acid adsorbed thereto are in contact with the washing solution should be in the defined time range.

In sub-step (w2), the magnetic particles with the nucleic acid bound thereto are incubated in the washing solution. The incubation time is adapted in order to remove as much contaminants as possible whilst avoiding significant loss of nucleic acid. The shorter the incubation time, the more contaminants may remain in the product. Thus, it may be preferable that the incubation time in step (w2), and/or the overall time for step (w), which is mostly determined by the incubation time, is at least 3, at least 5, at least 10, at least 20 or at least 30 seconds, or at least 1 minute. The higher the incubation time, the higher will be the risk of loss of nucleic acid. This applies all the more the shorter the nucleic acid is. Thus, it may be preferable that the incubation time and/or time of step (w) is 20 minutes or less, 10 minutes or less, 5 minutes or less, 2 minutes or less, 1 minute or less, 30 seconds or less, 20 seconds or less, 10 seconds or less, preferably 5 seconds. For example, the time could be between 3 seconds and 20 minutes, preferably between 5 seconds and 10 minutes, between 10 seconds and 5 minutes, between 20 seconds and 2 minutes or between 30 seconds and 1 minute. In such time spans, a relatively good balance between high loss of contaminants and high nucleic acid yield can be achieved.

In sub-step (w3), the magnetic particles with the nucleic acid bound thereto are separated from the washing solution. Preferably, the magnetic particles with the nucleic acid bound thereto are separated from the washing solution by application of a magnetic field. Preferably, the means of removing magnetic particles from the solution are the same throughout the entire process.

In the inventive method, the nucleic acid to be isolated is not specifically limited. The DNA could be genomic DNA (gDNA), plasmid DNA (pDNA), DNA fragments of any length, e.g. produced from restriction enzyme digestion, amplified DNA of any length produced by an amplification reaction such as the polymerase chain reaction (PCR) or nucleic acid sequence-based amplification (NASBA), DNA resulting from a bioprocess sample as obtained during the production of biotechnological compounds like biopharmaceuticals, or the like, wherein the DNA may be double-stranded or single-stranded. The term RNA as used in the present invention comprises but is not limited to total RNA, mRNA, rRNA or tRNA. Other suitable nucleic acids have been described above.

According to the invention, efficient removal of contaminants, such as non-target biomolecules, salts and organic solvents, is possible with nucleic acid of all chain lengths. For example, the DNA could have a chain length from 10 bp to 100 kbp, preferably from 500 bp to 50 kbp, or from 1 kbp to 20 kbp, the RNA having the corresponding chain lengths in bases or nucleotides.

In a preferred embodiment of the invention, the nucleic acid has a chain length of 2 kbp or more, preferably 5 kbp or more, or more preferably 10 kbp or more or the corresponding amount of bases or nucleotides, respectively. In a preferred embodiment, the nucleic acid may be genomic DNA or plasmid DNA. When the nucleic acid has a higher chain length like 10 kbp or above, more preferred 20 kbp or above most preferred 50 kbp or above, loss of nucleic acid in the washing step is considered negligible. Then, the washing step (w) may take a relatively long overall time in the range of minutes, such as up to 10 minutes. Yet, in particular for reasons of convenience a shorter overall washing time as indicated above may be preferred.

Some reduction of the yield may be observed with nucleic acids, in particular DNA having a relatively short chain length. However, loss of nucleic acid can then be avoided by decreasing the time of the washing step (w) and/or the incubation time in step (w2), for example to 2 minutes or less, 1 minute or less, 30 seconds or less, 20 seconds or less, 10 seconds or less, 5 seconds or less or 3 seconds. In principle, the shorter the DNA is, the less time washing step (w) should take. Under those circumstances the loss in nucleic acid may be in similar order of magnitude in the present method of the invention as in the rinsing procedure of the state of the art but with the additional advantage that more contaminations are removed resulting in nucleic acid of higher purity than in the state of the art.

In a preferred embodiment of the invention, the nucleic acid has a chain length of 30 kbp or less, 20 kbp or less, or 10 kbp or less, or a corresponding number of bases or nucleotides, wherein washing step (w) is carried out in 2 minutes or less, 1 minute or less, 30 seconds or less, 20 seconds or less, 10 seconds or less or preferably 5 seconds. Preferably the nucleic acid is DNA. In other preferred embodiments, the nucleic acid has a chain length of 5 kbp or less, or 3 kbp or less, 2 kbp or less, 1 kbp or less, more preferred at least 500 bp, or a corresponding number of bases or nucleotides, wherein the washing step is carried out in 1 minute or less, or 30 seconds or less, 20 seconds or less, 10 seconds or less, 5 seconds or less or 3 seconds. Preferably the nucleic acid is DNA.

Washing step (w) may be repeated as often as desired, for example may be repeated once, twice, three times or even more often. However, it was found that a very efficient removal of impurities is possible in a simple process with only a single washing step. Thus, it is highly preferred to carry out washing step (w) only once.

In a preferred embodiment, washing step (w) is carried out at a temperature of 30° C. or less, preferable between 0° C. and 30° C. If the temperature in washing step (w) is too high, nucleic acid may be released from the magnetic particles and get lost. In a preferred embodiment, it is carried out at room temperature, for example at from about 15° C. to 25° C. However, the sample may also be cooled, for example to 15° C. or less, most preferably 5° C. or less.

In a preferred embodiment, the method comprises additional washing steps, which are different from washing step (w). Preferably, such additional washing steps are carried out before washing step (w). Such additional washing steps may be carried out with conventional wash buffers or solutions comprising ethanol as described in the prior art. With such additional washing steps, a pre-purification can be achieved, such that levels of salt, alcohol and/or other contaminants are depleted. In a highly preferred embodiment, washing step (w) is the last washing step before an optional elution step.

In a preferred embodiment, before washing step (w) the magnetic particles with the nucleic acid adsorbed thereto are subjected to at least one pre-washing step (p) in which the washing solution is adapted to nucleic acid binding conditions. This means that in the pre-washing step (p), the salt concentration is relatively high and/or organic solvent is comprised. Such washing steps under binding conditions are commonly used in known methods to remove contaminants from the sample solution. Also in the inventive process, it may be advantageous to include such pre-washing steps (p) to remove contaminants, such as proteins or other cell components, or undesired low molecular weight compounds, from the sample solution.

In a preferred embodiment of the invention, before washing step (w), the magnetic particles with the nucleic acid adsorbed thereto are washed in at least one pre-washing step (p) with a washing solution, which is an aqueous solution having a total salt concentration above 500 mM and/or comprises an organic solvent. More specifically, in the prewashing step (p), the total salt concentration of the prewashing step (p) washing solution could be above 1 M or even above 2 M. In prewashing step (p), the organic solvent is preferably ethanol or isopropanol. Specifically, in the prewashing step (p), the washing solution may comprise a lower alcohol, such as ethanol or isopropanol, at a concentration of at least 10%, or at least 50% by weight, or pure alcohol.

In an embodiment of the invention, an additional washing step (p) is carried out, in which the magnetic particles with the bound nucleic acid, when fixated by the magnetic field, are rinsed with water, or with a low salt buffer as used in washing step (w), such that the nucleic acid remains bound to the particles. However, since washing step (w) is more efficient than such a rinsing step, it is preferred that such a rinsing step is not comprised.

In a preferred embodiment of the invention, after washing step (w) the nucleic acid is eluted from the magnetic particles with elution solution. Preferably, if elution is desired, the elution step is carried out directly after washing step (w). In other words, no other intermediate treatment steps, and especially washing steps, are carried out after washing step (w). The elution solution is preferably pure water, typically distilled water, or an elution buffer having a low salt concentration. Typically, elution buffer has a salt concentration of 25 mM or less, wherein the salt is generally a buffer salt, such as 10 mM TRIS. The pH of the elution solution and/or buffer is typically between 7 and 10, especially between 7.5 and 9. After elution, the nucleic acid preferably remains in the resulting elution solution while magnetic particles are removed from the elution solution by external force, such as centrifugation or a magnetic field. Yet, it is also suitable to elute the nucleic acid by the conditions applied in a subsequent downstream treatment and not in a separate elution step preceding the downstream treatment.

After the washing step (w), the target nucleic acid can be eluted form the magnetic beads with an elution solution. This elution step should be clearly distinguished from washing step (w), although the elution solution may be identical to the washing solution used in washing step (w). In the washing step (w), the nucleic acid essentially shall remain bound to the magnetic particles, whereas in the elution step the conditions are adjusted such that the nucleic acid is supposed to be eluted.

Preferably, elution is supported by mechanical force, extended incubation time and/or increased temperature. In a preferred embodiment, the elution of the nucleic acid from the magnetic particles is enhanced by applying a mechanical force. Specifically, elution may be accelerated by intensive stirring or shaking, especially at high speed, such as vortexing. The elution can be supported by incubating the magnetic particles with the nucleic acid adsorbed thereto in the elution solution for an extended time period, such as more than 5 minutes, more than 10 minutes or more than 60 minutes. Increasing the temperature may support the release of the nucleic acid from the magnetic particles. Thus, elution may be carried out at a temperature of 20° C. or higher, such as room temperature, or above 30° C.

The term 'magnetic particles' as used herein comprises magnetically responsive particles which are able to reversibly bind nucleic acids in the terms of the present invention, e.g. by ionic interaction or the like. Such particles are well known to a person skilled in the art. As used herein, the term 'magnetic' encompasses magnetic materials, such as ferromagnetic, ferrimagnetic, paramagnetic or superparamagnetic materials. These magnetic materials are part of the magnetic particles as described above and may be included in the particles by any suitable method.

In a preferred embodiment of the invention, the magnetic particles comprise silica. The silica could be in the form of silica gel, siliceous oxide, solid silica such as glass or diatomaceous earth, or a mixture of two or more of the above. The silica should be present at least in part on the surface of the beads. For efficient binding, it is preferred that the silica is present on the entire surface of the particles.

The magnetic particles may be silica coated magnetic particles. The term 'silica coated magnetic particles' refers to magnetic particles coated with silica. These particles are well known to the artisan. Any kind of silica coated magnetic particles is in principal suitable for the method of the present invention. Yet, preferably the magnetic particles are no anion exchange particles.

The silica gel is preferably chromatography grade silica gel, a substance which is commercially available from a number of different sources. Silica gel is most commonly prepared by acidifying a solution containing silicate, e.g. sodium silicate, to a pH of less than 10 or 11 and then allowing the acidified solution to gel (e.g. silica preparation discussion in Kurt-Othmer Encyclopedia of Chemical Technology, Vol. 6, 4th ed., Mary Howe-Grant, ed., John Wiley & Sons, pub., 1993, pp. 773-775).

The glass particles are preferably particles of crystalline silica (e.g., α-quartz, vitreous silica), even though crystalline silica is not formally 'glass' because it is not amorphous, or particles of glass made primarily of silica. Glass particles are also well known to the skilled person.

Siliceous-oxide coated magnetic particles are the most preferred form of silica magnetic particles used in the present invention. Siliceous-oxide coated magnetic particles are comprised of siliceous oxide coating a core comprising at least one particle of ferrimagnetic, ferromagnetic, superparamagnetic or paramagnetic material. The siliceous-oxide coated magnetic particles used in the present invention also have an adsorptive surface of hydrous siliceous oxide. The target nucleic acid, such as DNA or RNA, adheres to the adsorptive surface of the particles while other material from the source of the nucleic acid, particularly deleterious contaminants such as nucleases or the like, do not adhere to or co-elute from the siliceous-oxide coated magnetic particles together with the nucleic acid. Siliceous-oxide coated magnetic particles are well known to the artisan and are commercially available (e.g. MagAttract® magnetic particles, QIAGEN, Hilden, Germany).

The magnetic particles have the capacity to form a complex with the nucleic acid in the aqueous solution by reversibly binding the nucleic acid, e.g. by ionic interaction or the like. The present invention may be performed using any silica coated magnetic particles possessing the property of forming a complex with the nucleic acid. Even more preferably, the method of the present invention is performed using any form of siliceous-oxide coated magnetic particles, e.g. MagAttract® magnetic beads (QIAGEN, Hilden, Germany). The silica coated magnetic particles used in the methods of the present invention may be any one of a number of different sizes. Smaller silica magnetic particles provide more surface area per weight unit for adsorption, but smaller particles are limited in the amount of magnetic material which can be incorporated into such particles compared to larger particles.

The term 'salt' as used herein preferably refers to chaotropic and non-chaotropic salts. Typically, the sample solution and/or washing buffer for pre-washing steps (p) comprise a chaotropic salt and/or a non chaotropic salt. It was found that such salts can be efficiently removed in the inventive method by washing step (w).

In a preferred embodiment chaotropic salts are salts of chaotropic ions according to the 'Hoffmeister-Reihe'. Such salts are highly soluble in aqueous solutions. The chaotropic ions provided by such salts, at sufficiently high concentration in aqueous solutions of proteins or nucleic acids, cause proteins to unfold, nucleic acids to lose secondary structure or, in the case of double-stranded nucleic acids, melt (i.e. strand-separation). It is assumed that chaotropic ions show these effects because they disrupt hydrogen-bonding networks that exist in aqueous solutions and thereby make denatured proteins and denatured nucleic acids thermodynamically more stable than their correctly folded or structured counterparts. The chaotropic salt in the sample solution may be selected from the group of guanidinium isothiocyanate, guanidinium thiocyanate, guanidinium hydrochloride, sodium iodide, potassium iodide, lithium chloride, sodium perchlorate, sodium trichloroacetate or a mixture thereof. In a preferred embodiment of the invention, the non-chaotropic salt in the sample solution is selected from the group of sodium chloride, potassium chloride, ammonium chloride, calcium chloride, magnesium chloride or a mixture thereof.

The salt concentration in the sample solution of the present invention is preferably in a range of from 0.5 M and 10 M. With any salt used in the invention, it is desirable that the concentration of the salt, in any of the solutions in which the salt is employed in performing the method of the invention, remains below the solubility of the salt in the solution under all of the conditions to which the solution is subjected in performing the method of the invention. The concentration of the salt in the mixture must be sufficiently high to cause the biopolymer to adhere to the silica magnetic particles in the mixture, but not so high as to substantially denature or to degrade the nucleic acid, or to cause the nucleic acid to precipitate out of the aqueous solution. Proteins and large molecules of double-stranded DNA, such as chromosomal DNA, usually are stable at chaotropic salt concentrations between 0.5 M and 2 M, but are known to precipitate out of solution at chaotropic salt concentrations above about 2 M (e.g. U.S. Pat. No. 5,346,994, column 2, lines 56-63). Contrastingly, RNA and smaller molecules of DNA such as plasmid DNA, restriction fragments or PCR fragments of chromosomal DNA, or single-stranded DNA usually remain undegraded and in solution at chaotropic salt concentrations between 2 M and 5 M, which is well known to those skilled in the art. Thus, the salt concentration in a method according to the invention is dependent on the area of application and is apparent to those skilled in the art or is readily determinable.

If desired, the sample solution may comprise at least one additive for enhancing the binding to the magnetic particles. For example, the additive could be a non-ionic substance which is strongly hydratable and is selected from the group of ethylene glycol, tetraethylene glycol, polyalkylene glycol, cyclodextrin, carrageenan, dextran, dextran sulfate, xanthan, cellulose, hydroxypropyl cellulose, amylose, 2-Hydroxypropyl β-cyclodextrin, Agar Agar, or is a mixture thereof. Polyalkylene glycol is preferable but not restricted to polyethylene glycol, polypropylene glycol or a mixture thereof. In a preferred embodiment, the additive is polyethylene glycol. These additives are able to inhibit substantially the clustering of the magnetic particles in an aqueous solution at relatively low concentrations which allows for a trouble-free automated process, e.g. no clogging of pipette tips due to clustered magnetic particles occurs. Further information regarding the selection and use of such additives is provided in WO2005/021748 A1.

In a preferred embodiment of the invention, the method comprises the steps of (a) adding magnetic particles to a sample solution comprising the nucleic acid,
(b) incubating the sample solution of step (a) to adsorb the nucleic acid to the magnetic particles,
(c) applying a magnetic field to the sample solution to fixate the magnetic particles with the nucleic acid adsorbed thereto,
(d) removing the sample solution,
(e) washing the magnetic particles with a washing solution in a washing step (w) as defined above, and
(f) eluting the nucleic acid from said magnetic particles with an elution solution.

Preferably, steps (a) to (f) are carried out in consecutive order. Further steps may be included in the process, such as a pre-treatment of the original sample before step (a) for example in order to render the nucleic acid accessible for binding, like a lysis procedure releasing the nucleic acid, and/or in order to adjust the binding conditions. Before washing step (e), pre-washing steps (p) may be carried out in order to remove contaminants from the nucleic acid and magnetic particles. Washing step (e), i.e. washing step (w) under non-binding conditions, may be repeated until salt and organic solvent is removed as desired. In a specific embodiment, the method may basically consist of steps (a) to (f) and (p), each of which may be repeated if desired. In principle, methods with steps (a) to (d) and (f) are known in the art, and thus these process steps can be carried out as described in the prior art.

Preferably, the inventive process, or at least the steps of providing a sample solution, binding and washing, and optionally also elution, is/are carried out in a single tube. Typically, after the magnetic particles were treated with a solution and removed from the solution, the solution is also removed from the tube before the next step is carried out.

In a preferred embodiment of the invention, the method is an automated process. Since the inventive process is relatively simple to realize, it is especially suited for automation, for example with robots or work stations as commonly used in the prior art. Various methods of automated separation of magnetic particles are known from the art and all should be suitable for use in the present invention. As an example, a magnetic or magnetizable device can be inserted into the medium containing the magnetic particles, the magnetic particles are bound to the magnetic or magnetizable device, and the magnetic or magnetizable device is removed again. In a second embodiment of the inventive method the separation of medium and the magnetic particles, both aspirated into a pipette tip, is facilitated by a magnetic or magnetizable device which is brought into spatial proximity to the pipette tip. The magnetic particles are kept back in the pipette tip for example at the wall or the bottom of the tip when the medium is removed from the pipette tip. Automation of these two methods generally requires special technical means, e.g. a robot constructed especially for one of those methods. Yet, the methods may also be conducted manually.

A more general principal in removing magnetic particles is to bring a magnetic or magnetizable device into spatial proximity to the container containing the medium and the magnetic particles. The magnetic particles bind to the container wall and the medium can be removed without carry-over of magnetic particles.

Subject of the invention is also the use of an aqueous solution, which has a total salt concentration below 100 mM and does not comprise an organic solvent, as a washing solution for washing magnetic particles with nucleic acid adsorbed thereto in a method for isolating nucleic acid from a sample solution, wherein the magnetic particles with the nucleic acid adsorbed thereto are suspended in the washing solution. Preferably, the use is in a method as described above, and/or comprises specific steps or features as described above for the inventive method.

The nucleic acid using the method of the present invention may be obtained from biological material, such as eukaryotic or prokaryotic cells in culture or from cells taken or obtained from tissues, tumor cells, exosomes, multicellular organisms including animals and plants; body fluids such as blood, lymph, urine, feces, or semen; food stuffs; cosmetics; or any other source of cells or they may be extracellular. Further suitable sample materials have been described above. Some biopolymers, such as certain species of DNA or RNA are isolated according to the present method from the DNA or RNA of organelles, viruses, phages, plasmids, viroids or the like that infect cells. The cells could be bacterial cells, such as *E. coli* cells. Cells will be lysed and the lysate usually processed in various ways familiar to those skilled in the art to obtain an aqueous solution of DNA or RNA, to which the separation or isolation methods of the invention are applied. The DNA or RNA, in such a solution, will typically be found with other components, such as proteins, RNA (in the case of DNA separation), DNA (in the case of RNA separation), or other types of components. Further suitable biopolymers have been described above.

Before contacting the magnetic particles with the nucleic acid, it may be necessary to disrupt biological material in which the nucleic acid is contained. Regardless of the nature of the source of the nucleic acid, the nucleic acid to be isolated with the method of the present invention is provided in an aqueous solution comprising the nucleic acid and molecule different from the nucleic acids, e.g. cell debris, polypeptides, etc. When the nucleic acid material to be isolated using the methods of the present invention is contained within a cell, or tissue comprising cells, it is preferably first processed by lysing or disrupting the cell or tissue to produce a lysate (herein referred to as 'crude lysate'), and more preferably additionally processed by clearing the lysate of cellular debris (e.g. by centrifugation or vacuum filtration). Any one of a number of different known methods for lysing or disrupting cells to release nucleic acid materials contained therein are suitable for use in producing an aqueous solution from cells for use in the present invention. The method chosen to release the nucleic acid material from a cell will depend upon the nature of the cell containing the material. For example, in order to cause a cell with a relatively hard cell wall, such as a fungus cell or a plant cell, to release the nucleic acid material contained therein one may need to use harsh treatments such as potent proteases and mechanical shearing with a particle mill or a homogenizer, or disruption with sound waves using a sonicator. Contrastingly, nucleic acid material can be readily released from cells with lipid bilayer membranes such as *E. coli* bacteria or animal blood cells merely by suspending such cells in an aqueous solution and adding a detergent to the solution. Once the nucleic acid material is released from the cells lysed or disrupted as described above, cellular debris likely to interfere with the adhesion of the nucleic acid material to magnetic particles can be removed using a number of different techniques known from the art or combination of these techniques. The crude lysate is preferably centrifuged to remove particulate cell debris. Optionally, the supernatant is subsequently further processed by adding a second solution to the supernatant which causes a precipitation of other cell constituents, e.g. polypeptides, and then removing the precipitate from the resulting solution by centrifugation. In a preferred embodiment, the lysate thus obtained, or the supernatant, is used as the sample solution in the inventive process.

The nucleic acid may also be obtained an artificial source. The nucleic acid material can be the product of an amplification reaction, such as amplified DNA produced by the polymerase chain reaction (PCR) or nucleic acid sequence-based amplification (NASBA), or the like. The nucleic acid material can also be in the form of fragments of any length, e.g. produced from restriction enzyme digestion. The aqueous solution according to the invention may also be an aqueous solution comprising melted or enzymatically digested electrophoresis gel and nucleic acid material.

The nucleic acid isolated by the method of the present invention is suitable, without further isolation or purification, for analysis or further processing by molecular biological procedures, isolated nucleic acids can be analysed by, for example, sequencing, restriction analysis, or nucleic acid probe hybridization. Thus, the methods of the invention can be applied as part of methods, based on analysis of DNA or RNA, for, among other things, genotyping, diagnosing diseases, identifying pathogens, testing foods, cosmetics, blood or blood products, or other products for contamination by pathogens, forensic testing, paternity testing, and sex identification of fetuses or embryos or other preferably non-invasive prenatal testing (NIPT).

DNA or RNA isolated by the method of the present invention may be processed by any of various exonucleases and endonucleases that catalyse reactions with DNA or RNA, respectively, and, in the case of DNA, can be digested with restriction enzymes, which cut restriction sites present in the DNA. Restriction fragments from the eluted DNA can be ligated into vectors and transformed into suitable hosts for cloning or expression. Segments of the eluted DNA or RNA can be amplified by any of the various methods known in the art for amplifying target nucleic acid segments. If eluted DNA is a plasmid or another type of autonomously replicating DNA, it can be transformed into a suitable host for cloning or for expression of genes on the DNA which are capable of being expressed in the transformed host.

The inventive method solves the problem underlying the invention. An efficient method for isolation of nucleic acids is provided, which overcomes the drawbacks of known methods. Nucleic acid can be isolated in pure form and at high yield in a relatively simple and convenient process. Impurities, such as salts, organic solvents and contaminants from the sample solution are efficiently removed. Nucleic acids of different chain lengths can be isolated at high yield when adapting the incubation time in the washing step (w). The process does not require a time-consuming drying step for evaporation of organic solvents. The chemicals and components for washing step (w) are simple, because the washing solution can be water or low salt aqueous solution, and may even be identical to the elution solution.

Further aspects of the invention are shown in the figures.

FIG. 1 shows the results of example 3 in graphical form. Impurities in the eluents were analysed spectrometrically in the range of 220 to 350 nm. Dotted lines relate to two probes with DNA isolated by the triple wash method (comparative) according to example 1. Continuous lines relate to two probes with DNA isolated by a water-drop method according to the invention of example 2.

FIG. 2 shows the results of example 4 in graphical form. Impurities in the eluents were analysed spectrometrically in the range of 220 to 350 nm. Dotted lines relate to three probes with DNA isolated by the triple wash method (comparative). Continuous lines relate to a probe with DNA isolated by a water-drop method according to the invention.

Figure 5:
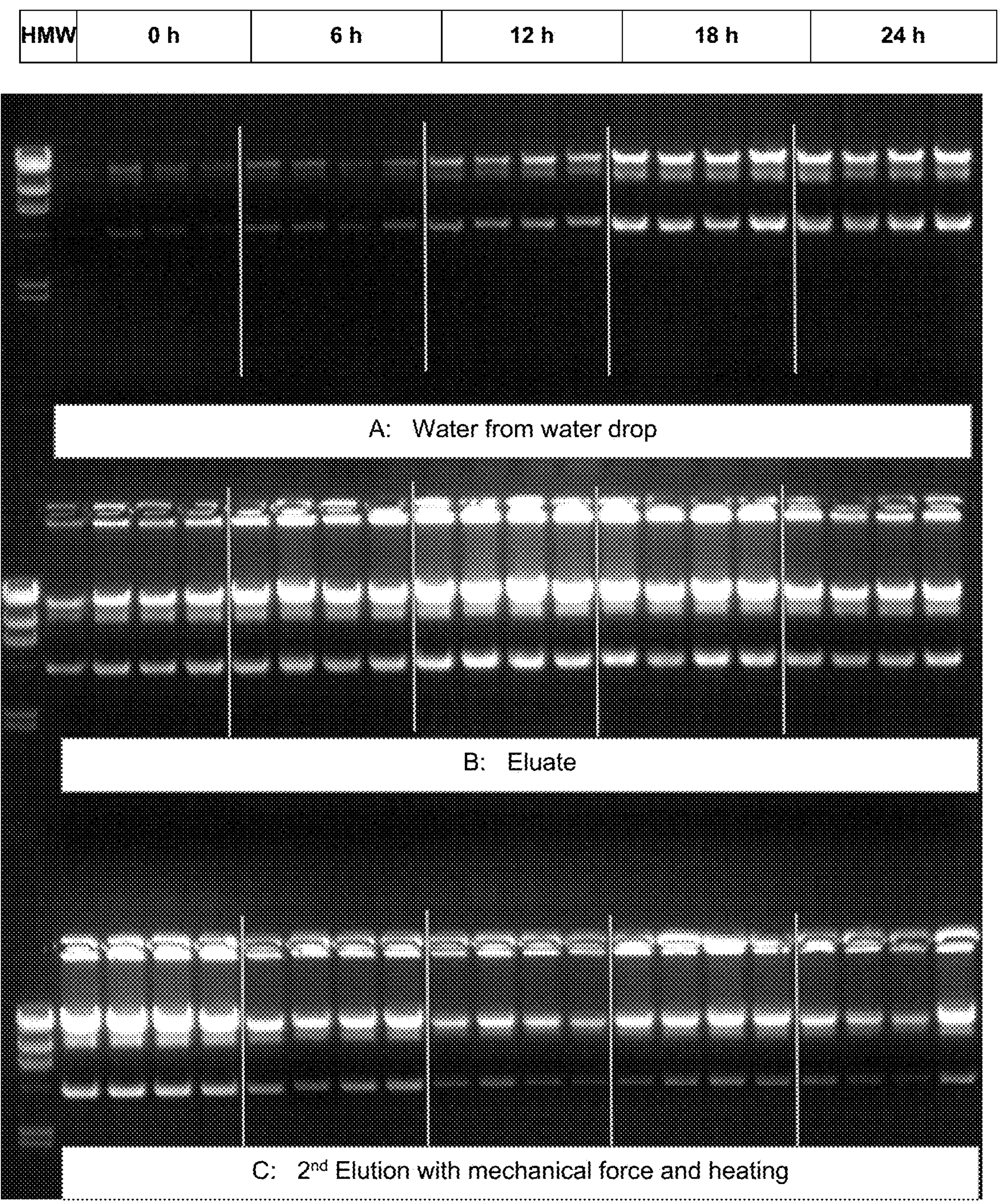

FIG. 5 shows an agarose gel of example 6 with plasmid pCMVβ isolated from *E. coli* according to example 2. DNA was analyzed from the eluate ("B: Eluate") and from the water used in the water-drop washing step ("A: Water from water-drop") after different incubation times of 0, 6, 12, 18 and 24 h. Further results are shown in section C from second elution step subsequent to the elution step in B., wherein mechanical force and moderate heat was applied to suspensions in the second elution step.

Figure 6:
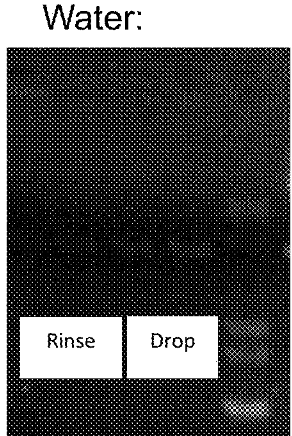
Figure 6:
Figure 6:
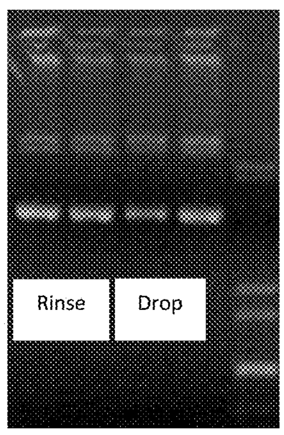
Figure 6:
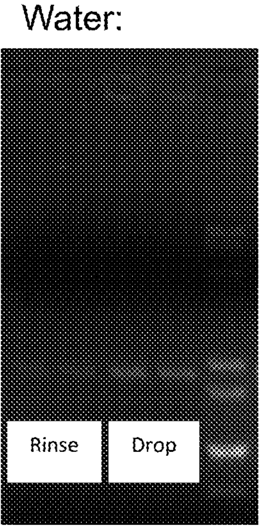
Figure 6:
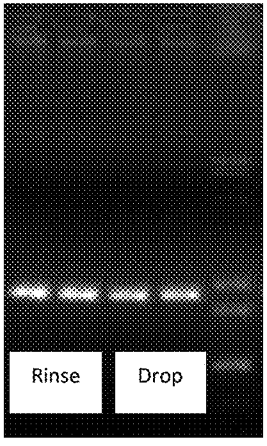

FIG. 6 shows an agarose gel of example 8 with plasmid pCMVβ and pUC21 isolated from *E. coli* according to examples 1 and 2. DNA was analyzed from the eluate ("elution") and from the water used in the water-drop washing step ("drop") or rinsing step ("rinse"), respectively.

EXAMPLES

Examples 1 and 2: Purification of DNA

DNA from bacterial cells was isolated according to the method of the invention (example 2) and to a prior art method (example 1). Conditions and working solutions are listed in table 1 below. Lysis of *E. coli* or whole-blood cells was performed according to the standard protocol with a kit available under the trademark QIAamp® (Qiagen AG, Hilden, Germany; cat no. 51304). DNA was purified with magnetic particles with the MagAttract® kit according to the standard protocol (Qiagen AG, Hilden, Germany; cat. no 67563) using a magnetic bead extraction platform (trademark Gilson Extractman®; Gilson Inc., Middleton, US/Salus Discovery). In the standard process of example 1, DNA was bound to magnetic silica particles from a buffer comprising a high concentration of chaotropic salt to establish binding conditions. Magnetic particles were separated from the sample solution by application of a magnetic field. Specifically, the magnetic particles were pulled out of the solution, followed by removal of sample solution. In lysis step 1 (table), the beads were only taken up and not suspended in the lysate again. The magnetic particles with DNA bound thereto were washed according to the protocol with various standard wash buffers by release of the particles into a washing buffer in a sample well, washing and re-attracting/collecting the magnetic particles with the bound DNA. Release was carried out by switching off, removing or relocating the magnetic field, such that the magnetic beads with nucleic acid bound thereto dropped into the solution below. In most washing steps, this cycle of binding the particles and "dropping" them was repeated in order to impose some mild mechanical force onto the particles. The number of "drops" of the magnetic beads in each step is also shown in the table.

In comparative example 1, before elution, the magnetic particles with DNA bound thereto, which were fixed to the sample tube by a magnetic force, were carefully rinsed with distilled water in step (5a). No further mechanical force, such as shaking or stirring, was applied in this washing step. In the following, this step is referred to as a "water-rinse"-step.

In the inventive example, the final water-rinse step was replaced by a final washing step (5b) in which the magnetic particles with DNA bound thereto were suspended in distilled water. The magnetic particles were released by removing the magnetic field and dropping the magnetic particles into the washing solution, followed by incubation for 5-10 seconds. No further mechanical force, such as shaking or stirring, was applied in this washing step. Subsequently, the magnetic particles with nucleic acids bound thereto were separated from the washing solution by re-initiating the magnetic force. In the following, such a washing step (w) is referred to as a "water-drop"-step, because the magnetic particles are dropped into the water for washing.

Elution was carried out by repeatedly dropping the beads into the elution solution in order to improve release of nucleic acid. Elution was supported by magnetic stirring for 3 minutes.

TABLE 1

Experimental conditions with buffer used and number of washing steps.

| Step | Buffer | Composition | Amount [μl] | Ex. 1 (comp): [number of drops/rinses] | Ex. 2 [number of drops] |
|---|---|---|---|---|---|
| 1 | Lysate | crude cell lysate<br>guanidinium HCl<br>ethanol | 400 | $3^d$ | 3 |
| 2 | wash MW1 | 1.5% Tween 20<br>7.5M guanidinium HCl<br>370 mM LiCl | 250 | $3^d$ | 3 |
| 3 | wash PE | 19 mM TRIS<br>80% ethanol | 120 | $3^d$ | 3 |
| 4 | wash PE | 19 mM TRIS<br>80% ethanol | 120 | $3^d$ | 3 |
| 5a | "water-rinse" | 19 mM TRIS<br>80% ethanol | 120 | $1^r$ | — |
| 5b | "water-drop" | distilled water | 120 | — | 1 |
| 6 | elution AE | 10 mM TRIS<br>0.5 mM EDTA | 120 | $10^d$ | 10 |

In each step, the magnetic particles were separated from the solution and the solution was removed.
The number of "drops", i.e. repeated release of magnetic particles into the same solution, is also indicated.
$^d$= drops,
$^r$= rinses

Example 3: Purity of Genomic DNA from *E. coli*

Figure 1:
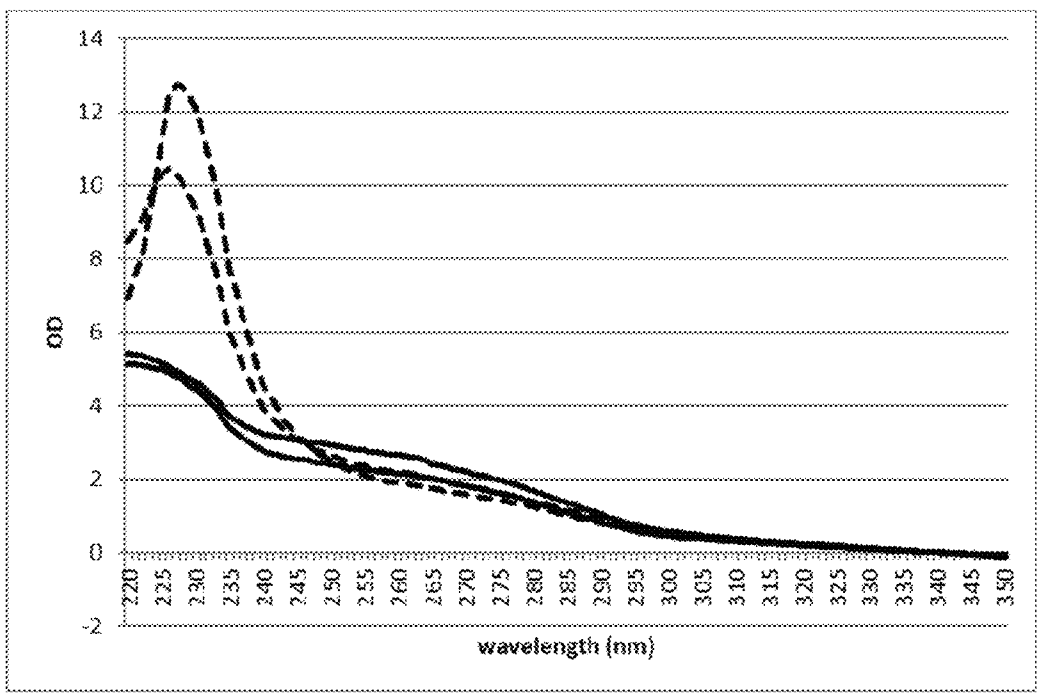

Impurities in *E. coli* genomic DNA prepared according to examples 1 and 2 above was determined spectrometrically. In order to wash off contaminants from the magnetic particles, elution was carried out by subjecting magnetic particles for three minutes to a magnetic stirrer. Impurities in the eluents were analyzed with a spectrometer in the range of 220 nm to 350 nm, wherein mostly salt carry-over is determined. The results are shown in FIG. 1. Dotted lines show values detected for two probes with DNA isolated according to a water-rinse protocol of example 1 (comparative). Continuous lines show values detected for two probes with DNA isolated according to a water-rinse protocol of example 2. A high OD value in the range between 220 and 245 nm is generally indicative of salt and other contaminants. The results demonstrate that the inventive process, with washing of magnetic particles with bound DNA in distilled water under non-binding conditions, removes far more contaminants than the comparative method with a water-rinse step of the prior art.

Example 4: Purity of DNA from Blood

DNA from human whole-blood was prepared according to the protocol of inventive example 2 and modified comparative example 1. In the process of example 1 described above, water-rinse step 5a (see table) was replaced by a third washing step with PE buffer. As in first and second PE buffer washing steps 3, 4, also in the third PE puffer washing step the magnetic particles were dropped three times into the solution. The purities of the isolated DNA products were compared. The aim was to determine if the additional washing step in the comparative process, with 3 drops into ethanol buffer PE, may remove impurities more efficiently than the inventive process with only one single drop of the particles into water.

Figure 2:
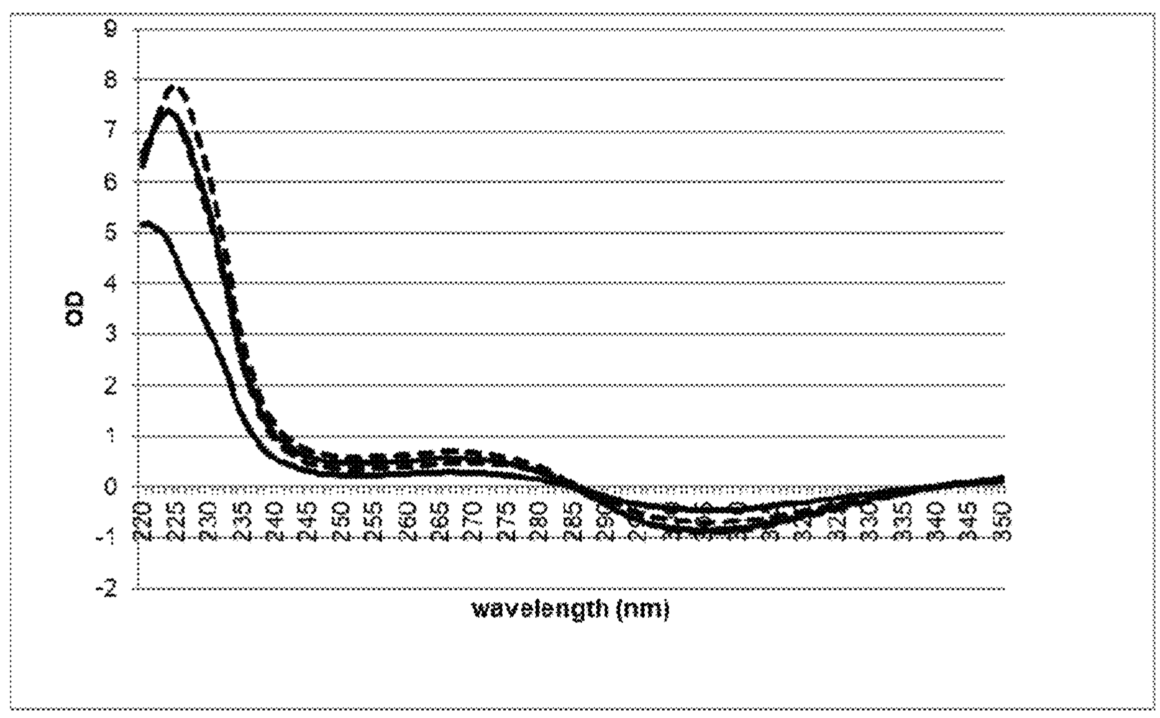

The results are shown in FIG. 2. Dotted lines relate to DNA isolated by the comparative triple wash method. Continuous lines relate to DNA of example 2 isolated by the water-drop method. The results demonstrate that the inventive process can remove significantly more contaminants from the sample than a conventional process. Each drop of the magnetic particles into washing buffer is associated with a gentle mechanical force that supports washing the magnetic particle-bound DNA free of contaminants. Following that logic, a triple sample drop into a wash buffer should be superior to a single drop in removing salts and other contaminants from the sample. Thus, it was unexpected that a single-drop into water cleaned up the DNA-sample similarly well or better than a triple washing step, wherein the particles were dropped into standard washing buffer.

Example 5: Yield of Genomic DNA from *E. coli*

Figure 3:
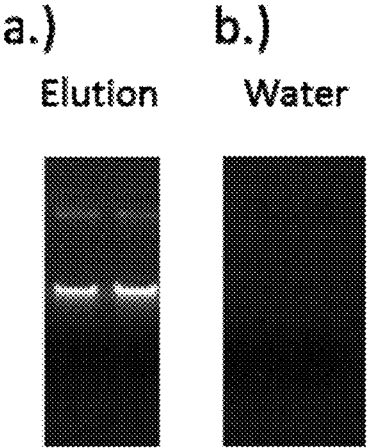
FIG. 3 shows an agarose gel of example 5 with genomic DNA isolated from *E. coli* according to example 2. DNA was analyzed from the eluate (lane a) and from the water used in the water-drop washing step (lane b).

The "water-drop" step in the inventive process was carried out with water, which usually imposes elution conditions to DNA bound to magnetic particles. Therefore, it was determined if a loss of DNA occurs in the method described in the examples above. Genomic DNA (gDNA; about 20 kbp length) was prepared from *E. coli* in the method of example 2 above. DNA from the eluate and from the remaining water used in the water-drop washing step was analyzed by agarose gel electrophoresis. The results are shown in FIG. 3. A strong gDNA band is visible for the product in the eluate (lane a), whereas DNA is not detectable in the water used in the water-drop step (lane b). The results demonstrate that DNA loss in the washing step of the inventive method, although carried out under non-binding conditions, is negligible.

Example 6: Yield of Plasmid DNA

DNA from *E. coli* cells carrying plasmid pCMVβ was prepared according to the standard protocol described in example 2. In the final washing step (water-drop step), the incubation time was 10 seconds. After incubation, the particles were re-collected and eluted as described in example 2.

Figure 4:
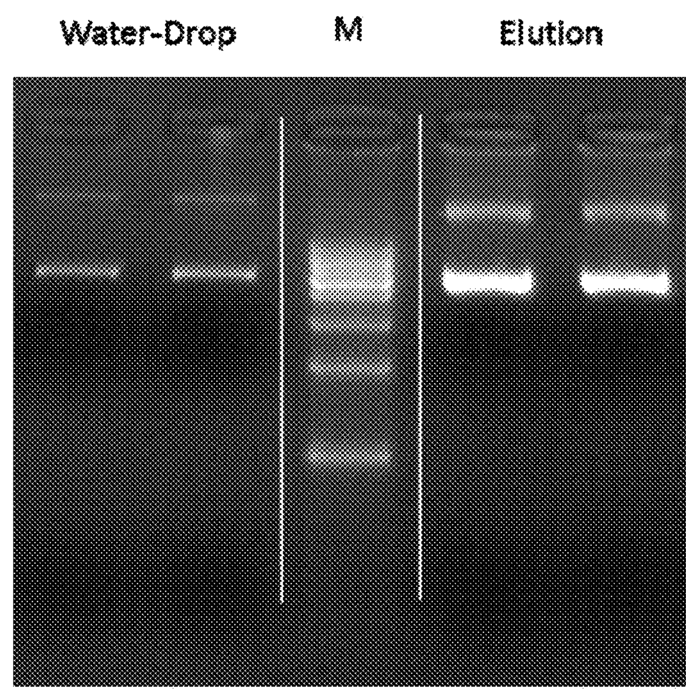
FIG. 4 shows an agarose gel of example 6 with plasmid pCMVβ isolated from *E. coli* according to example 2. DNA was analyzed from the eluate ("elution") and from the water used in the water-drop washing step ("water-drop").

DNA from the eluate and from the water used in the water-drop washing step was analyzed by agarose gel electrophoresis. The results are shown in FIG. 4. A strong plasmid DNA band is visible for the product ("elution", right lanes). A faint DNA band is also visible in the water used in the water-drop step ("water-drop", left lanes). The results demonstrate that a minor loss of plasmid DNA may occur in the washing step of the inventive method (water-drop step). These findings suggest that DNA yield depends on the length of the nucleic acids, such that shorter nucleic acids elute more easily from the silica magnetic particles. However, the absolute DNA loss is still low for plasmid DNA and thus the inventive method is applicable for producing excellent yields of highly pure plasmid DNA.

Example 7: Effect of Incubation Time and Mechanical Force on DNA Yield

DNA from *E. coli* cells carrying plasmid pCMVβ was prepared according to the standard protocol described in example 2. In the final washing step (water-drop step), the incubation time was varied from 0 to 24 hours. During that time period the particles were not moved or agitated but allowed to lie at the bottom of the tube After incubation, the particles were re-collected and eluted as described for example 2.

DNA from the eluate and from the water used in the water-drop washing step was analyzed by agarose gel electrophoresis. The results are shown in FIG. 5. Strong plasmid DNA bands are visible for the isolated DNA ("B: Eluate"). For water used in the washing step, only very faint DNA bands were visible after 0 and 6 hours ("A: Water from water drop"). The amount of DNA in water increased within 24 hours and reached significant levels. Overall, DNA elution increased over incubation time, although no mechanical force was applied to wash nucleic acids away from particles. The results suggest that loss of DNA can be decreased in the inventive process by reducing the incubation time.

In order to determine the effect of mechanical force and moderate heating in the elution step a further, i.e. second elution step was applied in which the magnetic particles were suspended for 3 minutes at 50° C. in a shaker at 1400 rpm. Such conditions represent common elution conditions which usually result in quantitative elution. Thereby, it could be verified if and how much DNA had still remained bound to the magnetic particles after the first elution procedure. FIG. 5 demonstrates that after the first elution procedure with rather moderate elution conditions still some DNA had remained bond to the magnetic particles. Yet, additionally applying mechanical force and moderate heating further releases the DNA from the magnetic particles ("C: Eluate after second elution procedure with mechanical force and moderate heating"). The results suggest that strong mechanical forces and heating should be avoided in the inventive washing step in order to obtain a high yield. After incubation for an extended time up to 24 hours, the amount of DNA in the eluate decreased, indicating that the DNA should have been quantitatively released.

Example 8 Comparison of Water-Rinse and Water-Drop for Plasmid DNA

DNA from *E. coli* cells carrying on one hand plasmid pCMVβ (about 7.2 kbp) and on the other hand plasmid UC21 (about 2.7 kbp) was prepared in parallel according to the standard protocols described in examples 1 and 2. In the final washing step (water-drop step), the incubation time was 5 seconds. After incubation, the particles were re-collected and eluted as described in examples 1 and 2. The results are shown in FIG. 6.

Short nucleic acids are known to elute from magnetic particles at a faster rate than long nucleic acids. It is assumed that this is due to the lower number of contact points between the nucleic acids and the beads. Therefore, it could have been expected that for the indicated plasmids the water-drop method of the present invention results in a tremendous loss of nucleic acid. Yet, surprisingly the results in FIG. 6 show that although the magnetic particles with the bound plasmid DNA are suspended in the washing solution, the loss of nucleic acid is very low and in a similar order of magnitude as is seen for the short and rather superficial rinsing procedure of the state of the art. Anyway, at the same time the purity of the plasmid DNA obtained with the water-drop washing procedure according to the present invention is increased compared to the rinsing procedure of the state of the art because due to the suspension of the particles more contaminations are removed. Consequently, the inventive method results in an improved purity without further loss of nucleic acid than in the state of the art.

The invention claimed is:

1. A method for isolating nucleic acid from a sample solution, wherein the nucleic acid is separated from the sample solution by adsorption to magnetic particles, followed by separation of the magnetic particles with the nucleic acid adsorbed thereto from the sample solution by application of a magnetic field, followed by at least one washing step (w), comprising (w1) suspending the magnetic particles with the nucleic acid adsorbed thereto in a washing solution, which is an aqueous solution, which has a total salt concentration below 100 mM and does not comprise an organic solvent, (w2) incubating the magnetic particles with the nucleic acid adsorbed thereto in the washing solution, and (w3) separating the magnetic particles with the nucleic acid adsorbed thereto from the washing solution, wherein the magnetic particles are dropped into the washing solution is step (w1) by switching off, removing or relocating the magnetic field.

2. The method of claim 1, wherein the nucleic acid is DNA, RNA or both.

3. The method of claim 1, wherein the washing solution has a total salt concentration below 25 mM.

4. The method of claim 1, wherein the washing solution consists of water.

5. The method of claim 1, wherein washing step (w) is carried out for 5 minutes or less.

6. The method of claim 1, wherein the nucleic acid has a chain length of at least 10 kb or kbp respectively.

7. The method of claim 1, wherein the nucleic acid has a chain length of less than 10 kb or kbp respectively, wherein washing step (w) is carried out for 2 minutes or less.

8. The method of claim 1, with one or more of the following characteristics being applied in washing step (w):

the magnetic particles with the nucleic acid bound thereto are not subjected to a mechanical force the magnetic particles with the nucleic acid bound thereto are not subjected to a mechanical force exerted oscillating and/or horizontally, the magnetic particles with the nucleic acid bound thereto are subjected to a mechanical force exerted vertically, the magnetic particles with the nucleic acid bound thereto are subjected to a magnetic force, the magnetic particles with the nucleic acid bound thereto are suspended in the washing solution without applying a mechanical force the magnetic particles with the nucleic acid bound thereto are suspended in the washing solution without applying a mechanical force exerted oscillating and/or horizontally the magnetic particles with the nucleic acid bound thereto are suspended in the washing solution with applying a mechanical force exerted vertically, the magnetic particles with the nucleic acid bound thereto are suspended in the washing solution with applying a magnetic force.

9. The method of claim 1, wherein before washing step (w), the magnetic particles with the nucleic acid adsorbed thereto are washed in at least one pre-washing step (p) with a washing solution, which is an aqueous solution having a total salt concentration above 500 mM and/or comprises an organic solvent.

10. The method of claim 1, wherein after washing step (w) the nucleic acid is eluted from the magnetic particles with an elution solution.

11. The method of claim 1, wherein the magnetic particles comprise silica.

12. The method of claim 1, wherein the sample solution comprises a chaotropic salt and/or an alcohol.

13. The method of claim 1, comprising the steps of (a) adding magnetic particles to a sample solution comprising the nucleic acid, (b) incubating the sample solution from step (a) to allow adsorption of the nucleic acid to the magnetic particles, (c) applying a magnetic field to the sample solution from step (b) to fixate the magnetic particles with the nucleic acid adsorbed thereto, (d) removing the sample solution from step (c), (e) washing the magnetic particles with a washing solution in a washing step (w) of claim 1, and (f) optionally eluting the nucleic acid from said magnetic particles with an elution solution.

14. The method of claim 1, wherein the method is an automated process.

* * * * *